US00PP31212P2

(12) United States Plant Patent
Van Swieten

(10) Patent No.: US PP31,212 P2
(45) Date of Patent: Dec. 10, 2019

(54) ***PHALAENOPSIS* ORCHID PLANT NAMED 'PHALGASEOT'**

(50) Latin Name: ***Phalaenopsis* hybrid**
Varietal Denomination: PHALGASEOT

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/350,443

(22) Filed: Nov. 16, 2018

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALGASEOT', particularly characterized by having white flowers with extra-large white lips, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALGASEOT'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGASEOT'.

The new *Phalaenopsis* plant is a product of a planned breeding program conducted by the inventor in Bleiswijk, The Netherlands. The objective of this breeding program was to create a new *Phalaenopsis* plant with numerous attractive white flowers with extra-large white lips, suitable for potted plant production.

The new *Phalaenopsis* plant 'PHALGASEOT' is a result of cross-pollination made by the inventor in April 2010 in Bleiswijk, The Netherlands, of the proprietary female, or seed parent, *Phalaenopsis* hybrid '21232-01' (unpatented) with the proprietary male, or pollen parent, *Phalaenopsis* hybrid '01-3403' (unpatented).

The new *Phalaenopsis* was selected by the inventor as a single plant within the progeny of the stated cross-pollination in a controlled greenhouse in Bleiswijk, The Netherlands, in February 2013. Asexual reproduction of the new *Phalaenopsis* plant by meristem tissue culture since 2015 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017. 'PHALGASEOT' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands, and can be used to distinguish 'PHALGASEOT' as a new and distinct variety of *Phalaenopsis* plant:

1) White flowers with extra-large white lips;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in October 2018. Colors in the photographs may differ from the color values cited in the detailed botanical description, which accurately describe the actual colors of the new variety.

DESCRIPTION OF THE NEW VARIETY

Figure 1:
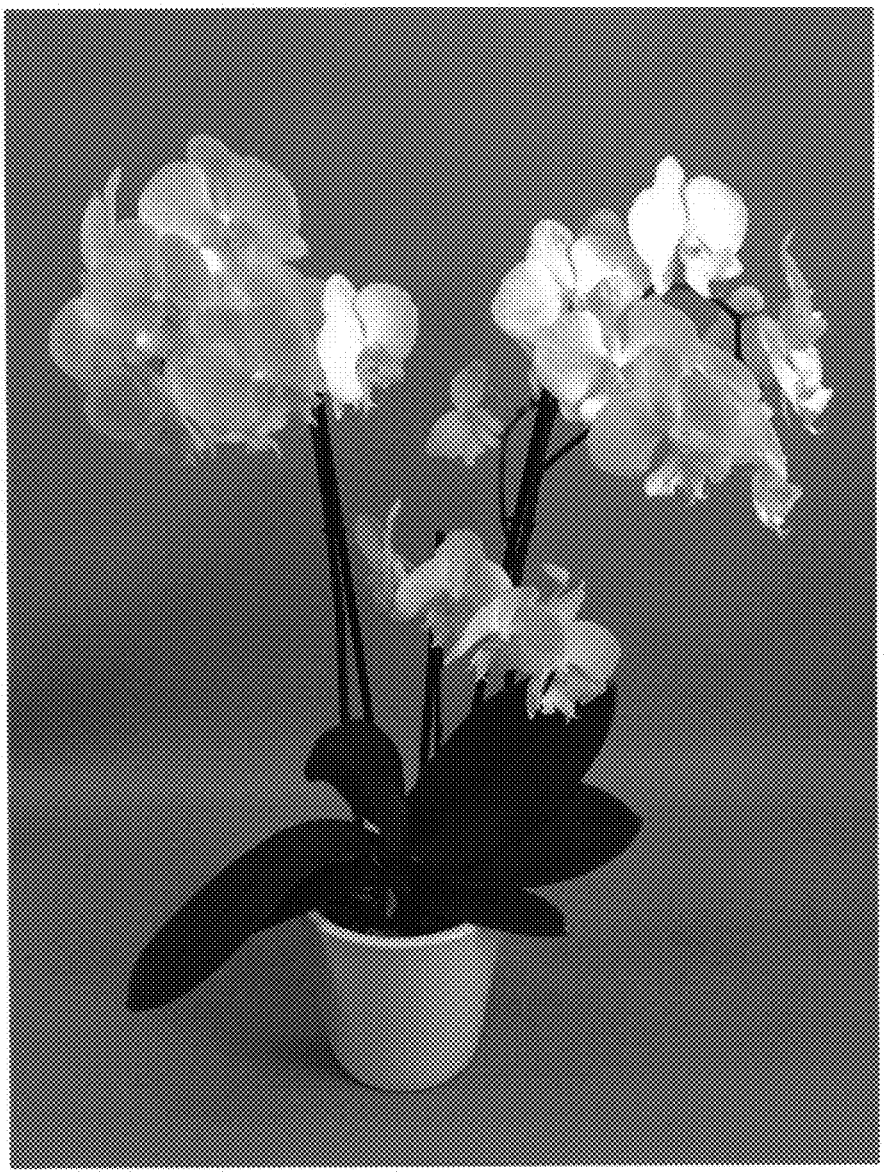
FIG. 1 shows the overall plant habit, including blooms and foliage of 'PHALGASEOT'.
Figure 2:
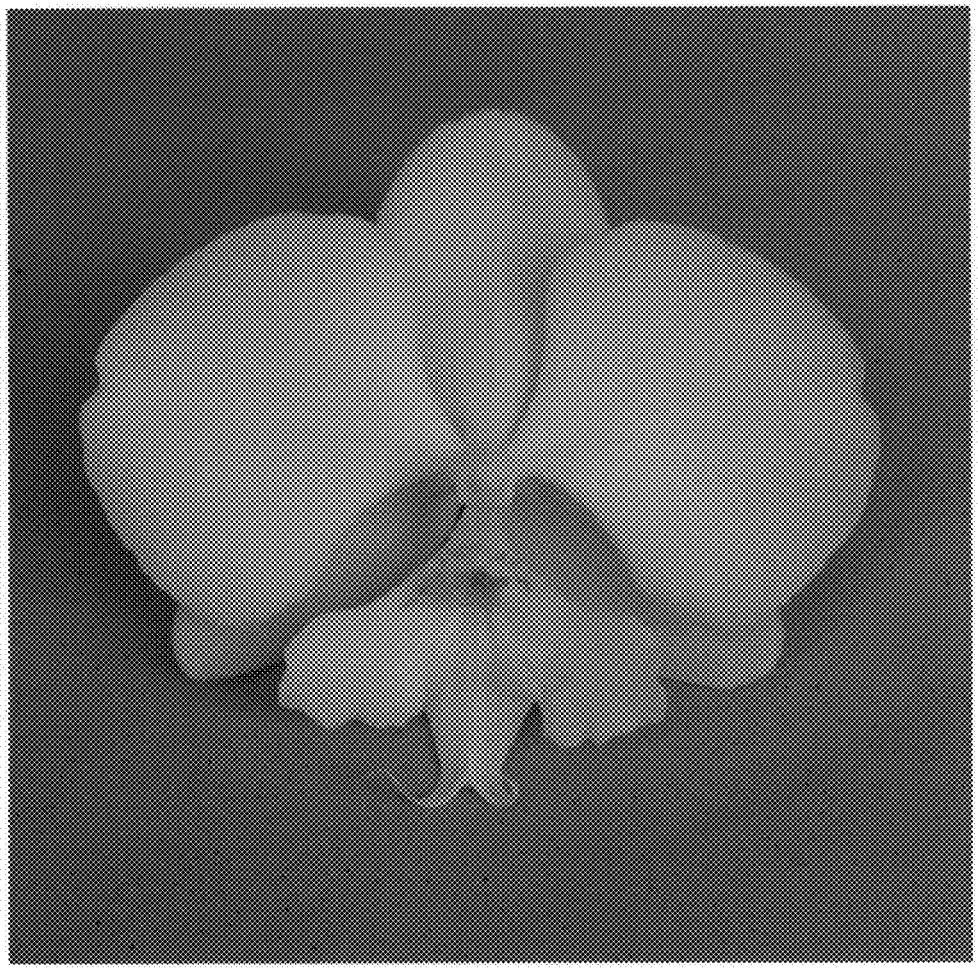
FIG. 2 shows a close-up of a flower of 'PHALGASEOT'.
Figure 3:
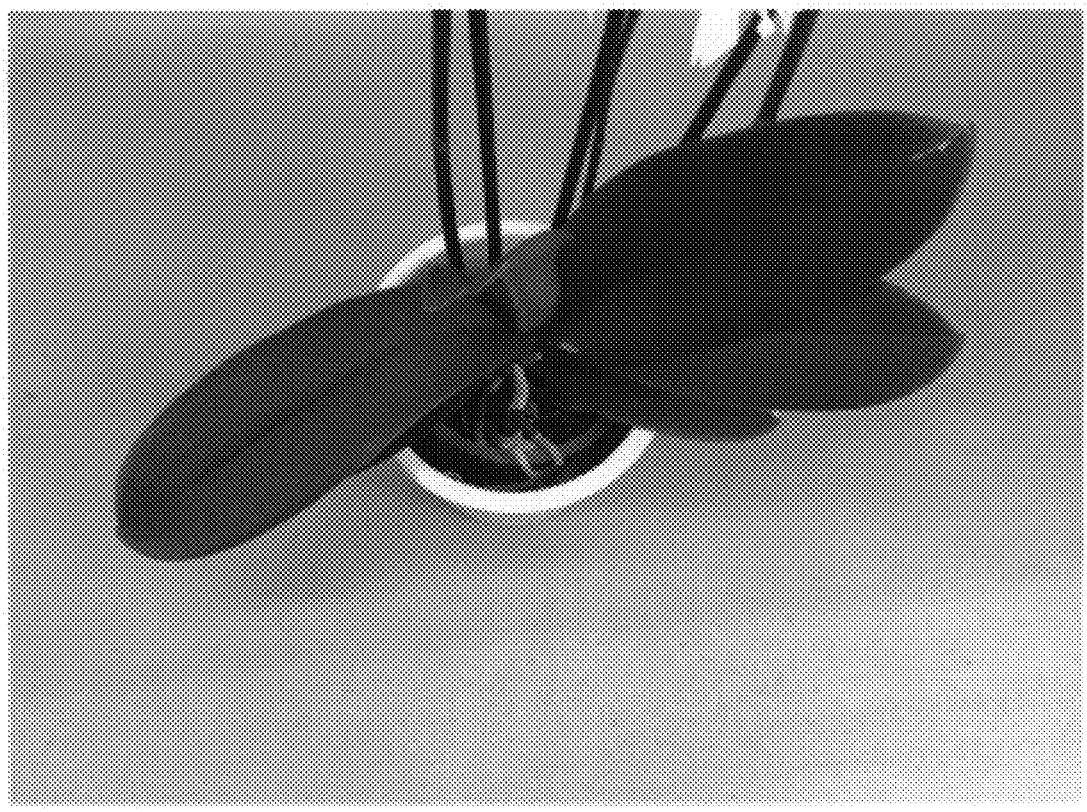
FIG. 3 shows an overhead view of the leaves of 'PHALGASEOT'.

The following detailed description sets forth the distinctive characteristics of 'PHALGASEOT'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-

6000 lux natural light in a greenhouse in Bleiswijk, The Netherlands. Observations and measurements were made in October 2018 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12 centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGASEOT'.

Parentage:

*Female parent*.—*Phalaenopsis* cultivar '21232-01' (unpatented).

*Male parent*.—*Phalaenopsis* cultivar '01-3403' (unpatented).

Propagation:

*Type*.—Meristem tissue culture.

Roots:

*Root description*.—Greyed-green (RHS 190B/C) colored roots with branching lateral roots having purplish-red (RHS N79C) colored root tips.

Plant:

*Commercial crop time to flowering*.—Following asexual propagation (in-vitro), the rooted cuttings grow for 20-24 weeks. After transplantation into 12 cm pots, the plants are finished after 48 to 50 weeks.

*Growth habit of peduncle*.—Upright to slightly pendant with panicle inflorescence.

*Height* (*from soil level to top of inflorescence*).—Approximately 53.0 cm to 58.0 cm.

*Width* (*measured from leaf tips*).—About 36.0 cm to 38.0 cm.

*Vigor*.—Strong.

Leaves:

*Mature leaves*.—Quantity per plant: 7 to 8 leaves are produced before flowering. Length (fully expanded): 18.0 cm to 22.0 cm. Width: 7.5 cm to 8.5 cm. Shape: Oblong. Base shape: Moderately elongated. Apex: Obtuse unequal. Leaf blade angle with the petiole (measured from the horizontal position): Between 15 degrees and 25 degrees. Leaf margin: Entire. Color: Upper surface: RHS 146A. Lower surface: RHS 146B. Texture (upper surface): Rough. Thickness: 2.4 mm to 2.6 mm. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—13 to 18.

*Length*.—53.0 cm to 58.0 cm.

*Diameter*.—6.3 mm to 6.8 mm.

*Strength*.—Strong.

*Aspect*.—Upright to slightly pendant.

*Texture*.—Smooth.

*Color*.—Mix of green (RHS 146B) and brown (RHS 200C).

*Internode length*.—6.5 cm to 7.5 cm.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 260.0 mm to 310.0 mm.

*Flowering time*.—First flowers can be expected 10 to 11 months after planting in a 12 cm (diameter) pot.

*Flower*.—Height: 75.0 mm to 80.0 mm. Diameter: 80.0 mm to 85.0 mm. Depth of lip: about 2.0 mm.

*Flower longevity*.—On the plant: 18 to 31 weeks.

*Fragrance*.—Absent.

*Flower bud*.—Average size: Medium to large. Length: 23.0 mm to 25.0 mm. Width: 17.0 mm to 19.0 mm. Shape: Egg shaped. Color: Light yellow-green (RHS 145C).

*Petals*.—Arrangement: Open/free. Shape: Semi-circular. Apex: Emarginated asymmetric. Margin: Slightly undulated. Length (from base to tip): 37.0 mm to 39.0 mm. Width: 44.0 mm to 46.0 mm. Color (when fully opened): Upper surface: Basic color: White (RHS NN155C). Over color: Absent. Lower surface: Basic color: White (RHS NN155C). Over color: Very light purple stripe (RHS 76C) in the middle.

*Dorsal sepal*.—Shape: Elliptic. Apex: Slightly emarginated symmetric. Margin: Entire. Length (from base to tip): 40.0 mm to 42.0 mm. Width: 27.0 mm to 29.0 mm. Color (when fully opened): Upper surface: Basic color: White (RHS NN155C). Over color: Absent. Lower surface: Basic color: White (RHS NN155C). Over color: Very light purple (RHS 76C).

*Lateral sepals*.—Shape: Ovate. Apex: Obtuse asymmetric. Margin: Entire. Length (from base to tip): 39.0 mm to 41.0 mm. Width: 21.0 mm to 23.0 mm. Color (when fully opened): Upper surface: Basic color: White (RHS NN155C). Over color: Light yellow-green (RHS 145C) at the base. Lower surface: Basic color: White (RHS NN155C). Over color: Slightly light yellow-green (RHS 145C) at the base and very light purple (RHS 76C) toward the apex.

*Labellum* (*lip*).—Overall shape: 3 lobed with callus at central junction of the lateral lobes and base of apical lobe. The apical lobe is terminated by 2 whiskers. Lateral lobes and apical lobe are connected.

*Lateral lobe*.—Margin: Undulated. Length: 24.0 mm to 26.0 mm. Width: 16.0 mm to 18.0 mm. Color: White (RHS NN155C) with few reddish-purple spots/stripes (RHS 72B) at the base.

*Apical lobe*.—Shape: Triangular. Margin: Entire. Length: 22.0 mm to 24.0 mm. Width: 24.0 mm to 26.0 mm. Color: Slightly light yellow-green (RHS 145C) at the base and white (RHS NN155C) toward whiskers. Whiskers: Present. Length of whiskers: 9.0 mm to 11.0 mm. Color of whiskers: White (RHS NN155C). Pubescence on the lip: Absent.

*Callus*.—Average size: Large. Height: 8.0 mm to 9.0 mm. Length: 7.0 mm to 8.0 mm. Width: 3.0 mm to 4.0 mm. Color: Light yellow-green (RHS 145C) with very small dots (RHS 72B).

Reproductive organs:

*Column*.—Length: 8.0 mm to 10.0 mm. Diameter: 4.9 mm to 5.4 mm. Color: White (RHS NN155C).

*Pollinia*.—Quantity: 2. Diameter: 1.0 mm to 1.2 mm. Color: Orange-yellow (RHS 21A).

*Ovary*.—Length: 10.0 mm to 12.0 mm. Diameter: 2.3 mm to 2.6 mm. Color: Light yellow-green (RHS 145C) and very light purple (RHS 76C) toward the flower.

*Pedicel*.—Length: 35.0 mm to 37.0 mm. Diameter: 2.8 mm to 3.1 mm. Color: Yellow-green (RHS 146D) at the base; light yellow-green (RHS 145C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGASEOT' differs from female parent plant '21232-01' (unpatented) in that 'PHALGASEOT' has light yellow-green (RHS 145C) calluses with very small dots (RHS 72B), whereas '21232-01' has yellow (RHS 17A) calluses with RHS 8A on the sides and spots/stripes (RHS 175A). Additionally, 'PHALGASEOT' has smaller flowers than '21232-01'.

'PHALGASEOT' differs from male parent plant '01-3403' (unpatented) in that 'PHALGASEOT' has white columns and emarginated asymmetric petal apexes, whereas '01-3403' has light reddish-purple columns and rounded petal apexes. Additionally, 'PHALGASEOT' has larger flowers than '01-3403'.

'PHALGASEOT' is most similar to the commercial *Phalaenopsis* plants named 'PHALGOSEP' (U.S. Plant patent application Ser. No. 15/999,891) and 'PHALGATYH' (U.S. Plant patent application Ser. No. 15/999,887). 'PHALGASEOT' differs from the commercial variety 'PHALGOSEP' in that 'PHALGASEOT' has emarginated asymmetric petal apexes, whereas 'PHALGOSEP' has rounded asymmetric petal apexes. Additionally, 'PHALGASEOT' has shorter leaves and longer whiskers than 'PHALGOSEP'.

'PHALGASEOT' differs from the commercial variety 'PHALGATYH' in that 'PHALGASEOT' has emarginated asymmetric petal apexes and flowers with an upper surface basic color of white, whereas 'PHALGATYH' has rounded asymmetric petal apexes and flowers with an upper surface basic color of very light purple.

I claim:

1. A new and distinct variety of *Phalaenopsis* plant named 'PHALGASEOT', substantially as described and illustrated herein.

* * * * *